(12) United States Patent
Lamoureux et al.

(10) Patent No.: US 10,307,613 B2
(45) Date of Patent: *Jun. 4, 2019

(54) INTERNAL BODY CAVITY THERAPEUTIC APPLICATOR ARRANGEMENTS AND METHODS FOR USING THE SAME

(71) Applicants: MEMORIAL SLOAN-KETTERING CANCER CENTER, New York, NY (US); GC MEDTECH LLC, Hialeah, FL (US)

(72) Inventors: Gary A. Lamoureux, Woodbury, CT (US); Gil'Ad N. Cohen, Tenafly, NJ (US); Karyn Goodman, New York, NY (US)

(73) Assignees: MEMORIAL SLOAN-KETTERING CANCER CENTER, New York, NY (US); GC MEDTECH LLC, Hialeagh, FL (US)

( * ) Notice: Subject to any disclaimer, the term of this patent is extended or adjusted under 35 U.S.C. 154(b) by 53 days.

This patent is subject to a terminal disclaimer.

(21) Appl. No.: 15/425,365

(22) Filed: Feb. 6, 2017

(65) Prior Publication Data

US 2017/0143991 A1    May 25, 2017

Related U.S. Application Data

(63) Continuation of application No. 14/348,781, filed as application No. PCT/US2012/058326 on Oct. 1, 2012, now Pat. No. 9,561,080.
(Continued)

(51) Int. Cl.
*A61N 5/10* (2006.01)
*A61B 1/018* (2006.01)
(Continued)

(52) U.S. Cl.
CPC ............ *A61N 5/1002* (2013.01); *A61B 1/018* (2013.01); *A61B 34/20* (2016.02); *A61B 90/10* (2016.02);
(Continued)

(58) Field of Classification Search
CPC ............ A61M 25/003; A61M 25/1011; A61M 2025/0008; A61M 2025/1013;
(Continued)

(56) References Cited

U.S. PATENT DOCUMENTS 5,653,683 A    8/1997 D'Andrea
6,251,059 B1   6/2001 Apple et al.
(Continued)

FOREIGN PATENT DOCUMENTS

JP    2001-515773      9/2001
JP    2009-232882 A   10/2009
(Continued)

OTHER PUBLICATIONS

Examiner's report dated Aug. 2, 2017 for Canadian National Phase application No. 2,550,621.
(Continued)

*Primary Examiner* — Christine H Matthews
*Assistant Examiner* — Joshua Daryl D Lannu
(74) *Attorney, Agent, or Firm* — Hunton Andrews Kurth LLP

(57) ABSTRACT

An apparatus for providing at least one treatment to at least one tissue having a first structural arrangement configured to expand a first portion at a distal end of the apparatus, a second structural arrangement configured to expand a second portion at the distal end and at least one lumen associated with at least one of the first structural arrangement and/or the second structural arrangement. The first structural arrangement and/or the second structural arrangement can
(Continued)

be configured to position the at least one lumen at a particular position with respect to the tissue. A tip is configured to aid in the insertion of the apparatus into the tissue(s).

20 Claims, 5 Drawing Sheets

Related U.S. Application Data

(60) Provisional application No. 61/541,715, filed on Sep. 30, 2011.

(51) Int. Cl.
*A61M 25/00* (2006.01)
*A61M 25/10* (2013.01)
*A61M 25/01* (2006.01)
*A61B 90/00* (2016.01)
*A61B 34/20* (2016.01)
*A61M 25/09* (2006.01)
*A61B 90/10* (2016.01)

(52) U.S. Cl.
CPC ........... *A61B 90/39* (2016.02); *A61M 25/003* (2013.01); *A61M 25/0026* (2013.01); *A61M 25/0067* (2013.01); *A61M 25/0105* (2013.01); *A61M 25/09* (2013.01); *A61M 25/1011* (2013.01); *A61N 5/1007* (2013.01); *A61N 5/1014* (2013.01); *A61B 2090/101* (2016.02); *A61M 2025/004* (2013.01); *A61M 2025/0008* (2013.01); *A61M 2025/1013* (2013.01); *A61M 2025/1093* (2013.01); *A61N 2005/1003* (2013.01); *A61N 2005/1018* (2013.01)

(58) Field of Classification Search
CPC .......... A61M 2025/1093; A61M 25/09; A61M 25/00; A61N 5/1014; A61N 5/1007; A61N 5/1002; A61N 2005/1003; A61B 1/018; A61B 2019/207; A61B 19/54; A61B 19/5244; A61B 19/20
See application file for complete search history.

(56) References Cited

U.S. PATENT DOCUMENTS

| | | | |
|---|---|---|---|
| 6,958,052 | B1 | 10/2005 | Charlton |
| 7,357,770 | B1 | 4/2008 | Cutrer |
| 2003/0032851 | A1 | 2/2003 | Apple et al. |
| 2005/0080313 | A1 | 4/2005 | Stewart |
| 2006/0100475 | A1 | 5/2006 | White et al. |
| 2008/0108859 | A1 | 5/2008 | Cutrer et al. |
| 2009/0254064 | A1 | 10/2009 | Boatman |
| 2010/0048977 | A1 | 2/2010 | Sing et al. |
| 2010/0069878 | A1* | 3/2010 | Parsai ............... A61M 25/1002 604/500 |
| 2010/0191034 | A1 | 7/2010 | Cutrer et al. |
| 2010/0331601 | A1 | 12/2010 | Partridge |

FOREIGN PATENT DOCUMENTS

| | | |
|---|---|---|
| JP | 2011-509798 | 3/2011 |
| WO | WO 99/27985 A1 | 6/1999 |
| WO | WO 2008/124149 A1 | 10/2008 |

OTHER PUBLICATIONS

International Search Report for International Patent Application No. PCT/US2012/058326 dated Jan. 24, 2013.
Written Opinion for International Patent Application No. PCT/US2012/058326 dated Jan. 24, 2013.
Supplementary European Search Report for European Application No. 12835312 dated Jun. 10, 2015.
Chinese Office Action and Search Report for Chinese Application No. 201280059335 dated Sep. 6, 2015.
Chinese Office Action and Search Report for Chinese Application No. 201280059335.X dated Apr. 22, 2016.
Japan Office Action for Japense Application No. 2014-533476 dated Aug. 2, 2016.
Communication pursuant to Aide 94(3) EPC dated Nov. 8, 2018 for European patent Application No. 12835312.5.

* cited by examiner

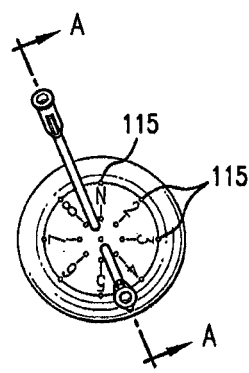
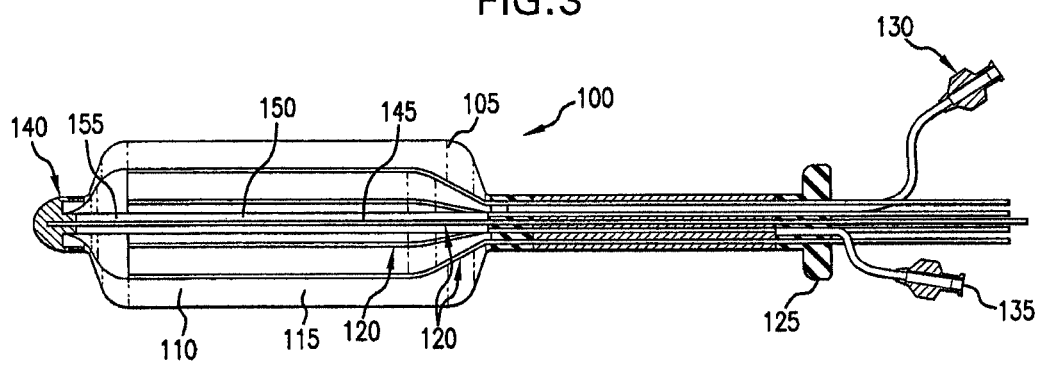

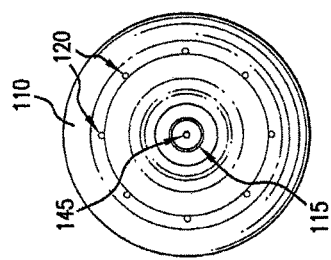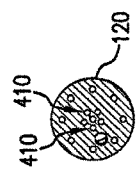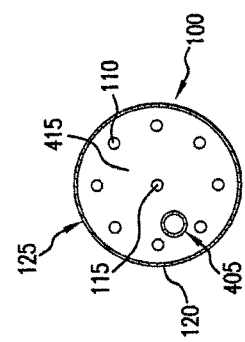

INTERNAL BODY CAVITY THERAPEUTIC APPLICATOR ARRANGEMENTS AND METHODS FOR USING THE SAME

CROSS-REFERENCE TO RELATED APPLICATIONS

This present application is a continuation of U.S. National Phase patent application Ser. No. 14/348,781 filed on Mar. 31, 2014 which is issuing as U.S. Pat. No. 9,561,080 on Feb. 7, 2017, and also relates to and claims the benefit and priority from International Patent Application No. PCT/US2012/058326 filed on Oct. 1, 2012, and further claims priority from pursuant to 35 U.S.C. § 119(e) from U.S. Provisional Patent Application Ser. No. 61/541,715 filed on Sep. 30, 2011, the entire disclosures of which are hereby incorporated herein by reference.

FIELD OF THE DISCLOSURE

Exemplary embodiments of the present disclosure relate to apparatus and methods for treating internal tissue disorders, and more particularly, to apparatus and methods for the treatment of such disorders by direct application of radiation and/or pharmacological therapy to areas within a patient's body.

BACKGROUND INFORMATION

Internal tissue disorders (e.g., cancer) can be a result of genetic malformations or can arise from sickness or trauma. Such disorders can typically be treated, for example, with the application of pharmaceuticals (e.g., directly or systemically), by the application of tissue altering forces (e.g., radiotherapy), or by surgical intervention.

In certain instances, the choice and application of treatments can be distinctly separate, and can be performed in a prescribed order and fashion. However, it can be beneficial to provide an optimal combination of treatments directly to the site of the disorder within the same procedure. Such treatment options, however, are generally not easily achievable.

Thus, it may be beneficial to provide a treatment option directly to the site of the disorder that can be combined with other treatment options. Accordingly, it is the object(s) of the present disclosure include addressing and/or overcoming at least some of the deficiencies described herein above.

SUMMARY OF EXEMPLARY EMBODIMENTS

These and other objects of the exemplary disclosure can be achieved by provision of a treatment apparatus and method for using the treatment apparatus in at least one tissue of a patient. For example, the treatment apparatus can comprise a first structural arrangement configured to expand a first portion of a distal end of the apparatus, a second structural arrangement configured to expand a second portion of the distal end and at least one lumen associated with at least one of the first structural arrangement or the second structural arrangement. The first structural arrangement and/or the second structural arrangement can be configured to position the at least one lumen at a particular position with respect to the tissue. A tip at the distal end can be configured to aid in the insertion of the apparatus into the tissue(s). The lumen(s) can be located between the first structural arrangement and the second structural arrangement. The second structural arrangement can be configured to expand the tissue(s), and the first structural arrangement can be configured to positions the lumen(s) at a particular position with respect to the tissue(s).

In certain exemplary embodiments, the lumen(s) can comprise at least 8 lumens, e.g., equally spaced circumferentially around the distal end. One of the lumens can be labeled to provide a reference point for all of the lumens. One of the lumens can configured to receive a treatment option, which can be a radiation source or a pharmacological agent. A second lumen can be located substantially in the center of the apparatus. The apparatus can be configured to be guided into the tubular structure using a guide, which can be an endoscope, a cable or a wire. A proximal end of the apparatus can have distance markers spaced equally apart, which can be detected by an imaging arrangement which can aid in the insertion of the apparatus. The first structural arrangement and/or the second structural arrangement can be a baffle. The first structural arrangement and/or the second structural can be filled with sterile water or air. A single baffle source can inflate the first structural arrangement and the second structural arrangement, or two baffles sources can be included, one each for filling the first structural arrangement and the second structural arrangement. The apparatus can be an anorectal applicator, an esophageal applicator, a sigmoid applicator, and/or a colon applicator.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying drawings showing illustrative embodiments of the present disclosure, in which:

FIG. 1 is a side view of the exemplary applicator according to an exemplary embodiment of the present disclosure;

FIG. 2 is a cross-section of the exemplary applicator of FIG. 1 according to an exemplary embodiment of the present disclosure;

FIG. 3 is a partial cross-section of the exemplary applicator from FIG. 1 according to an exemplary embodiment of the present disclosure;

FIGS. 4A and 4B are cross-sectional views of the exemplary applicator from FIG. 1 according to an exemplary embodiment of the present disclosure;

Figure 5:
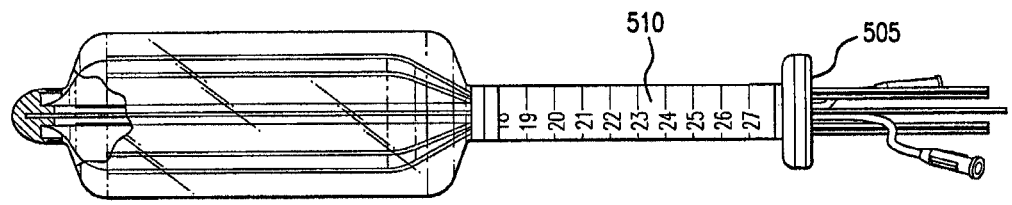
FIG. 5 is a side view of the exemplary applicator from FIG. 1 according to an exemplary embodiment of the present disclosure.

Throughout the figures, the same reference numerals and characters, if any and unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described exemplary embodiments without departing from the true scope and spirit of the subject disclosure.

DETAILED DESCRIPTION OF EXEMPLARY EMBODIMENTS

Exemplary embodiments of the present disclosure may be further understood with reference to the following description and the related appended drawings. The exemplary embodiments of the present disclosure relate to an applicator that can be used to treat internal tissue disorders by targeting multiple treatments directly to the internal tissue disorder. For example, the exemplary applicator can use a plurality of lumens to provide the treatment directly to the disorder depending on where in the tubular structure the disorder is located. Those having ordinary skill in the art will understand that the exemplary embodiments of the present disclosure can be implemented in any tubular structure in the body of a patient (e.g., the rectum, the nose, the lungs, the GI track, etc.)

FIG. 1 shows a side view of an exemplary applicator/arrangement/apparatus 100 according to an exemplary embodiment of the present disclosure in an inflated form, for delivering treatment to an internal tissue disorder. Exemplary applicator 100 can have a distal, or treatment, end 105 that can be inserted into the tubular structure and a proximal end 125 (e.g., a handle or handle extension). Distal end 105 can include a tip 140 which can be configured to aid in the insertion of exemplary applicator 100 into the tubular structure. For example, tip 140 can be smaller than the width of distal end 105, and can increase in size towards distal end 105. With the aid of a lubricant (e.g., liquid, gel or the like), exemplary applicator 100 can be inserted into a tubular structure by inserting tip 140 into the tubular structure until the desired location is reached.

Distal end 105 can include an outer baffle 110, an inner baffle 115, and a plurality of source lumens 120 which can be located circumferentially around distal end 105 in one or both of outer baffle 110 and inner baffle 115 or separately therefrom. Additionally, a single center source lumen 145 can be provided which can extend substantially through the center of distal end 105. Inner baffle 110 and outer baffle 115 can inflate distal end 105 in order to move source lumens 120 closer to the targeted treatment area. Exemplary applicator 100 can be fitted upon a guide 150 (e.g., an endoscope, a cable, a guide wire, or the like). A center channel 155 can be used to glide the apparatus over guide 150, for example, from a proximal to a distal location after guide 150 is placed. Accordingly, exemplary applicator 100 can be positioned, e.g., via cable and/or wire 150, at the location of the treatment site, and can be held stationary or otherwise maintained at the location of treatment. Alternately or in addition, exemplary applicator 100 can be fixed to the endoscope, cable, or guide wire, and can be introduced simultaneously with the endoscope, cable or guide wire placement at the treatment site.

Source lumens 120 can provide radial access to an intended treatment site for the placement of therapeutic agents, such as, e.g., high dose radiation, chemotherapy, etc. Further, there can be additional tubes along the axis that are connected to outer baffle 110 and inner baffle 115. As can be seen in FIG. 2, inner baffle 115 can be located between the center core opening and source lumens 120, facilitating the expansion and separation of source lumens 120 or it can be located outside of source lumens 120 when viewed from the front. Inner baffle 115 can be composed of a compliant or non-compliant material, and can be configured or structured to position the tubes at a predetermined position. Outer baffle 110 can be disposed over the outside of the treatment tubes thus facilitating an expansion in order to fixate and align the treatment area of the device relative to the wall of the intended treatment site. Outer baffle 110 can be composed of a compliant or non-compliant material (e.g., an elastomer material), and can position the treatment delivery tubes at one or more positions and/or locations relative to the treatment site.

Outer baffle 110 can be configured to expand the tubular structure exemplary applicator 100 has been inserted into. Inner baffle 115 can then be used to expand source lumens 120 to be in close proximity of the wall of the tubular structure.

Outer baffle 110 can include a restrictor arrangement which can be configured and/or structured to contour outer baffle 110 in order to better position and target the treatment to the treatment site. The exemplary restrictor arrangement can include various rings, bands, sleeves, tongues, etc. that can facilitate control over the shape and contour the baffle for the proper position and targeting of the treatment of the anatomical structure. According to certain exemplary embodiments of the present disclosure, the restrictor arrangement can be slidable to position the restrictor over exemplary applicator 100. Alternatively or in addition, the shape and contour of outer baffle 110 can be facilitated through the use of multiple baffles. In certain exemplary embodiments of the present disclosure, outer baffle 110 and/or inner baffle 115 can be filled with sterile water and have a drain mechanism for easier device removal. In addition to utilization of a low coefficient of friction material for the inner channel, the outer most material can also have a lubricious characteristic.

Inner baffle 115 can be configured to open to a predetermined diameter, and set the array of source lumens 120 equidistant from one another. Outer baffle 110 can be configured to provide a determinable water layer between the radiation source(s) and the treatment site, facilitating a dosimetric optimization. Source lumens 120 can be provided or sandwiched between, inner baffle 110 and outer baffle 120, and can therefore be provided in a straight and/or parallel configuration with respect to the treatment site thus providing a definitive "Effective Treatment Zone". Radiopaque markers at the proximal and distal ends of the Effective Treatment Zone, as well as along the axis of the tubes, can be used to facilitate an accurate placement confirmation with standard imaging techniques. One or more additional tubes (e.g., center source lumen 145) along the center axis of the device can provide another mechanism of administering an optimized treatment dose such as a pharmacological agent. The center tube can also accept a removable stiffening mandrel providing added rigidity during device insertion.

FIG. 3 shows a partial cross-section of exemplary applicator 100. Exemplary applicator 100 can have any suitable number of source lumens (e.g., 8 as shown in FIG. 3). Source lumens 120 can be labeled by number (e.g., 1, 2, 3 . . . ) or by letter (e.g., a, b, c . . . ). Alternatively, a combination of letters and numbers such as the letter N and the numbers 2-8 can be used. The use of the letter N can facilitate the user of exemplary applicator 100 to maintain a relative direction of exemplary applicator 100.

FIGS. 4A and 4B show cross-sections of exemplary applicator 100. Exemplary applicator 100 can have a single inflation lumen configured to inflate both outer baffle 110 and inner baffle 115 at the same time, or the single lumen can be configured to separately inflate outer baffle 110 and inner baffle 115. Alternatively, exemplary applicator 100 can have an outer baffle inflation lumen configured to only inflate outer baffle 110, and one or more inner baffle inflation lumens configured to inflate inner baffle 115 (e.g., outer baffle infusion port 130 inflates outer baffle 110 and inner baffle infusion port 135 inflates inner baffle 115). As shown, exemplary applicator 100 can have 8 source lumens 120, which can be equally spaced circumferentially, such that a 45 angle is formed by an angle composed of a line connecting the center of exemplary applicator 100 to a first lumen and a line connecting the center of exemplary applicator 100 to a second lumen adjacent to the first lumen. Alternatively, more or less than 8 source lumens can be used, and source lumens 120 can be spaced unequally apart.

The deployed diameter of outer baffle 110 can be any suitable size (e.g., 6 centimeters), although not limited thereto. Additionally, the deployed diameter of inner baffle 115 can be of any suitable size (e.g., 4 centimeters), although not limited thereto.

Exemplary applicator 100 can have a sliding lockable anal positioning flange 505 to provide both secure placement of the apparatus and relief of pressure or discomfort should the applicator be pressing against the distal sigmoid wall. Lockable anal positioning flange 505 can include a proximal base plate which can have, for example, a device orientation arrangement and tube numbering on its face, which can facilitate the user knowing which direction corresponds to the N marker for one of the source lumens as described above. This exemplary configuration can facilitate the user being able to determine the approximate position of each source lumen 120 inside exemplary applicator 100, facilitating the user to choose the best source lumen 120. Exemplary applicator 100 can also have a plurality of distance marker 510 which can facilitate the user knowing the approximate distance exemplary applicator 100 has been inserted into the tubular structure. This can benefit the user and the patient when exemplary applicator 100 is being inserted into as the user can mark the distance of the first insertion, and the same distance can be used in subsequent insertions, limiting any discomfort.

The inner surface of source lumens 120 and the outer surface of exemplary applicator 100 can include a lubricious quality for ease of both of either patient and/or source insertion. Additional exemplary modifications can include hemispherical baffles, external drug elution ports, etc.

In an exemplary embodiment of the present disclosure, the overall length of exemplary applicator 100 can be approximately 28.54 centimeters. The over length of distal end 105 can be approximately 16.3 centimeters. The overall length from tip 140 of exemplary applicator 100 to the end of source lumens 120 can be approximately 3.3 centimeters. It should be noted that the above exemplary lengths are for illustrative purposes only, and other lengths, greater or less than the above, can be used depending on the size of the tubular structure to be entered and the size of the patient.

Figure 6A:
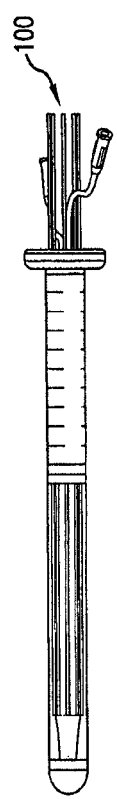
FIGS. 6A-6D are side views of the exemplary applicator of FIG. 1 at different inflation points according to an exemplary embodiment of the present disclosure.
Figure 6B:
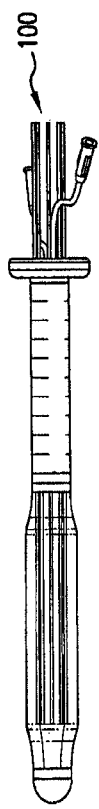
Figure 6C:
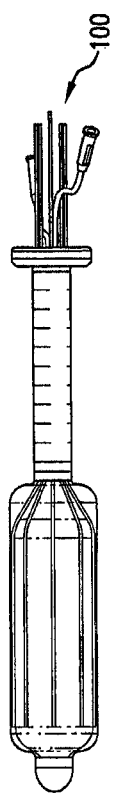
Figure 6D:
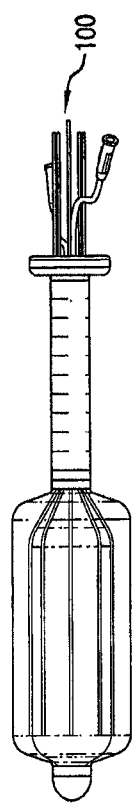

Exemplary applicator 100 can be configured to be uniform in size prior to being inflated, as seen in FIG. 6A. After exemplary applicator 100 has been inserted to the desired location, the baffles can be expanded, inflating exemplary applicator 100 to its desired inflation size, as seen in FIGS. 6B-D.

According to certain exemplary embodiments of the present disclosure, exemplary applicator 100 can be used as an esophageal applicator and can be a "Rail Guided" arrangement. Exemplary applicator 100 can have a tri-lumen inner tube surrounded by a single baffle. One of the lumens (e.g., three lumens) can include a through-hole or bore for facilitating device to fit over a guide wire facilitating placement. The second lumen can be provided for filling the baffle(s). The third lumen can be closed at the end of the Effective Treatment Zone, and can be the conduit for the high dose radiation (HDR) wire. The outer diameter of the esophageal applicator arrangement can preferably be less than approximately 8 millimeters for insertion. When in place, the baffle(s) can be inflatable up to, for example, approximately 2 centimeters in diameter or extension. Exemplary applicator 100 arrangement can also include a slidable locking base plate which can include a mouthpiece and the length can be adjustable up to, for example, approximately 130 centimeters (e.g., markings on the proximal handle). The exemplary Effective Treatment Zone can be, for example, approximately 15 centimeters with parallel orientation to the treatment site.

According to another embodiment of the present disclosure, exemplary applicator 100 can be or include a sigmoid applicator arrangement and a colon applicator arrangement, or exemplary applicator 100 can be a hybrid of an anorectal applicator and an esophageal applicator arrangement. For example, exemplary applicator 100 can apply the working mechanisms of the anorectal applicator with the "Rail Guided" exemplary feature of the esophageal applicator. Because of the path of the sigmoid and the colon, exemplary applicator 100 can be longitudinally flexible in order to make the various turns, while preferably also being axially stiff enough to be pushed to the treatment site. Accordingly, this can be where the "Rail Guidance" configuration can be employed.

Exemplary applicator 100 can be designed such that any radiation source can be inserted into source lumens 120, including multiple radiations sources at a time. The radiation source can be positioned in the source lumen nearest to the internal tissue disorder such that a radiation does can be maximally applied to the internal tissue disorder, and yet minimally applied to the surrounding area, thus limiting the patient's exposure to the radiation, and any possible side effects.

Exemplary applicator 100 can be used in conjunction with an imaging apparatus (e.g., X-ray, MRI etc.) to aid in the positioning of exemplary apparatus 100 nearest to the internal tissue disorder. This can greatly reduce the setup and treatment time. Markers on exemplary applicator 100 can be made from "exotic" materials to easily be seen on imaging apparatuses.

Figure 7:
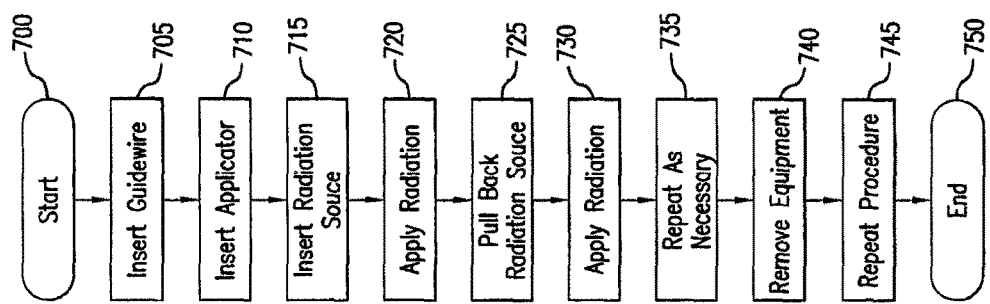
FIG. 7 is a method for treating a patient using the exemplary applicator of FIG. 1 according to an exemplary embodiment of the present disclosure.

FIG. 7 shows an exemplary method for treating a patient using exemplary applicator 100. After the location of an internal tissue disorder has been determined, the method begins at procedure 700. At procedure 705, guide wire 150 can be inserted into the patient to the desired site of the internal tissue disorder. At procedure 710, exemplary applicator 100 can be inserted into the patient to the desired site using guide wire 150 and exemplary applicator 100 can be inflated to the desired size. At procedure 715, a radiation source can be inserted into one of source lumens 120 that corresponds to the location closest to the internal tissue disorder. At procedure 720, radiation can be applied to the internal tissue disorder. At procedure 725, the radiation source can be pulled back, and an additional radiation does can be applied at procedure 730. At procedure 735, the process of pulling back the radiation source and applying the radiation source can be repeated, if preferred or as necessary. At procedure 740, most or all of the equipment, including exemplary applicator 100, can be removed from the patient. At procedure 745, a further procedure of applying a radiation source using exemplary applicator 100 can be repeated and at procedure 750, the method of treating the patient can end.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. In addition, all publications and references referred to above can be incorporated herein by reference in their entireties. In addition, certain terms used in the present disclosure, including the specification, drawings and claims thereof, can be used synonymously in certain instances. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it can be explicitly incorporated herein in its entirety.

What is claimed is:

1. An apparatus for providing at least one treatment to at least one tissue, comprising:
    a first inflation structure configured to expand a first portion at a distal end of the apparatus;
    a second inflation structure configured to expand a second portion at the distal end; and
    at least one lumen extending from a proximal end of the apparatus to the distal end, and having an opening at the proximal end, wherein the at least one lumen is located between and separate from the first inflation structure and the second inflation structure;
    wherein the first inflation structure is configured to position the at least one lumen at a particular position with respect to the at least one tissue based on an expansion of the first portion, and wherein the second inflation structure is configured to position the at least one lumen at the particular position with respect to the at least one tissue based on an expansion of the second portion, and
    wherein at least one of the first inflation structure or the second inflation structure is a baffle filled with at least one of sterile water or air.

2. The apparatus of claim 1, further comprising a tip portion provided at the distal end and configured to facilitate an insertion of the apparatus into the at least one tissue.

3. The apparatus of claim 1, wherein the second inflation structure is configured to expand the at least one tissue.

4. The apparatus of claim 1, wherein the at least one lumen is configured and structured to provide a radiation source through the opening.

5. The apparatus of claim 1, wherein the at least one lumen comprises at least eight lumens equally spaced apart circumferentially around the distal end.

6. The apparatus of claim 5, wherein one of the lumens is visibly labeled or marked to provide a reference point for all of the lumens.

7. The apparatus of claim 1, wherein the at least one lumen is configured to receive a treatment option.

8. The apparatus of claim 7, wherein the treatment option is at least one of a radiation source or a pharmacological agent.

9. The apparatus of claim 1, further comprising a second lumen located substantially in a center of the apparatus.

10. The apparatus of claim 1, wherein the apparatus is configured to be guided into a tubular structure using at least one of at least an endoscope, a cable or a wire.

11. The apparatus of claim 1, further comprising markers at least one of spaced equally apart at the proximal end of the apparatus to determine a distance at which the apparatus is inserted into the at least one tissue or spaced along the distal end which are provided to be detected by an imaging device to aid in insertion of the apparatus.

12. The apparatus of claim 1, wherein the first inflation structure and the second inflation structure are baffles filled with at least one of the sterile water or the air, and further comprising at least one of a single baffle source for inflating the first inflation structure and the second inflation structure or two baffle sources, one of the baffle sources provided for inflating the first inflation structure and the other of the baffle sources provided for inflating the second inflation structure.

13. The apparatus of claim 1, further comprising at least one of a single source for inflating the first inflation structure and the second inflation structure or two sources, one of the sources provided for inflating the first inflation structure and the other of the sources provided for inflating the second inflation structure.

14. The apparatus of claim 1, wherein the apparatus includes at least one of an anorectal applicator, an esophageal applicator, a sigmoid applicator or a colon applicator.

15. A method for treating a patient using an apparatus configured to provide at least one radiation treatment to at least one tissue of the patient, comprising:
    inserting the apparatus into the at least one tissue;
    expanding a first portion at a distal end of the apparatus using a first inflation structure;
    expanding a second portion at the distal end using a second inflation structure;
    positioning at least one lumen at a particular position with respect to the at least one tissue, wherein at least one lumen extends from a proximal end of the apparatus to the distal end, and has an opening at the proximal end, and wherein the at least one lumen is located between and separate from the first inflation structure and the second inflation structure;
    inserting at least one radiation source into the at least one lumen; applying, using the at least one radiation source, the at least one radiation treatment directly to an internal portion of the at least one tissue which includes a disorder;
    contracting at least one of the first inflation structure or the second inflation structure; and
    removing the radiation source and the apparatus from the at least one tissue;
    wherein at least one of the first inflation structure or the second inflation structure is a baffle.

16. The method of claim 15, further comprising using an imaging device to aid in an insertion of the apparatus.

17. The method of claim 16, further comprising providing markers at least one of spaced along the distal end capable of being detected by the imaging device to aid in the insertion of the apparatus or spaced equally apart at the proximal end of the apparatus to determine a distance of an insertion of the apparatus into the at least one tissue.

18. The method of claim 17, further comprising marking a further distance marker on the apparatus, and reinserting the apparatus only to a position of the further marked distance marker.

19. The method of claim 15, wherein the baffle is filled with at least one of sterile water or air.

20. The method of claim 15, wherein both of the first inflation structure and the second inflation structure are baffles filled with at least one of sterile water or air.

\* \* \* \* \*